United States Patent [19]

Miller

[11] 4,205,953
[45] Jun. 3, 1980

[54] CALCIUM MAGNESIUM ANALYZER

[75] Inventor: Edward G. Miller, East Haven, Conn.

[73] Assignee: Olin Corporation, New Haven, Conn.

[21] Appl. No.: 863,183

[22] Filed: Dec. 22, 1977

[51] Int. Cl.² .................... G01N 21/26; G01N 21/28
[52] U.S. Cl. .................................. 23/230 R; 422/62; 422/81
[58] Field of Search ................... 23/230 R, 230 A; 422/67, 81, 119, 62

[56] References Cited

U.S. PATENT DOCUMENTS 4,043,756  8/1977  Sommervold .................... 422/67 X

OTHER PUBLICATIONS

McCullough et al., "High-Precision Measurement of Calcium in Cadmium Phosphate Plant Materials, and a Micro-Method for both Calcium and Magnesium in Brine", "Automation in Analytical Chem.", Technicon Corp., (1967), pp. 233-238.

*Primary Examiner*—R. E. Serwin
*Attorney, Agent, or Firm*—Bruce E. Burdick; Thomas P. O'Day

[57] ABSTRACT

A method and apparatus for automatically measuring calcium and magnesium concentrations of less than about 500 parts per million in a liquid solution is disclosed by repeatedly automatically trapping a single sample, colorimetrically analyzing the trapped sample and displaying a corresponding calcium and magnesium concentration reading.

12 Claims, 6 Drawing Figures

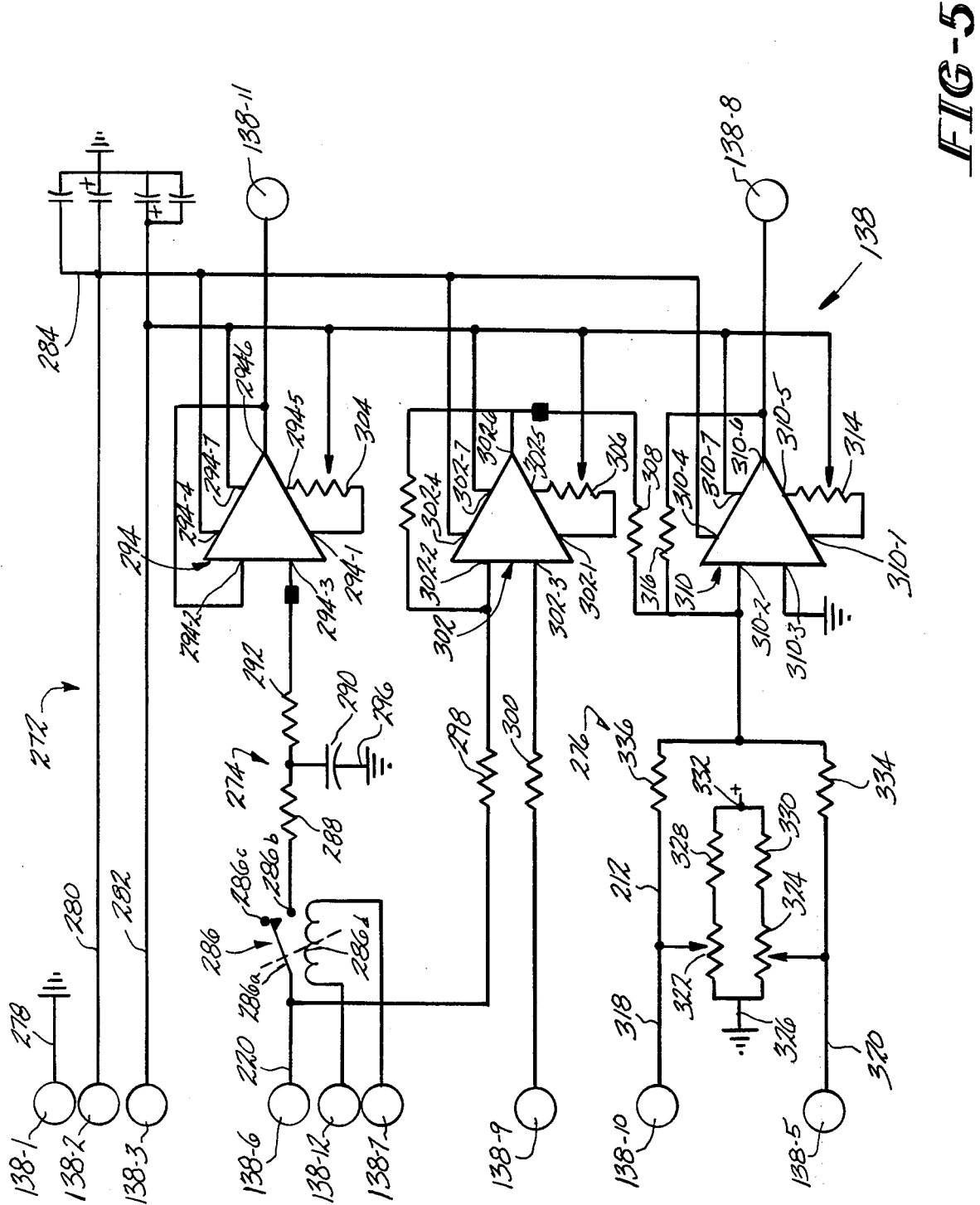

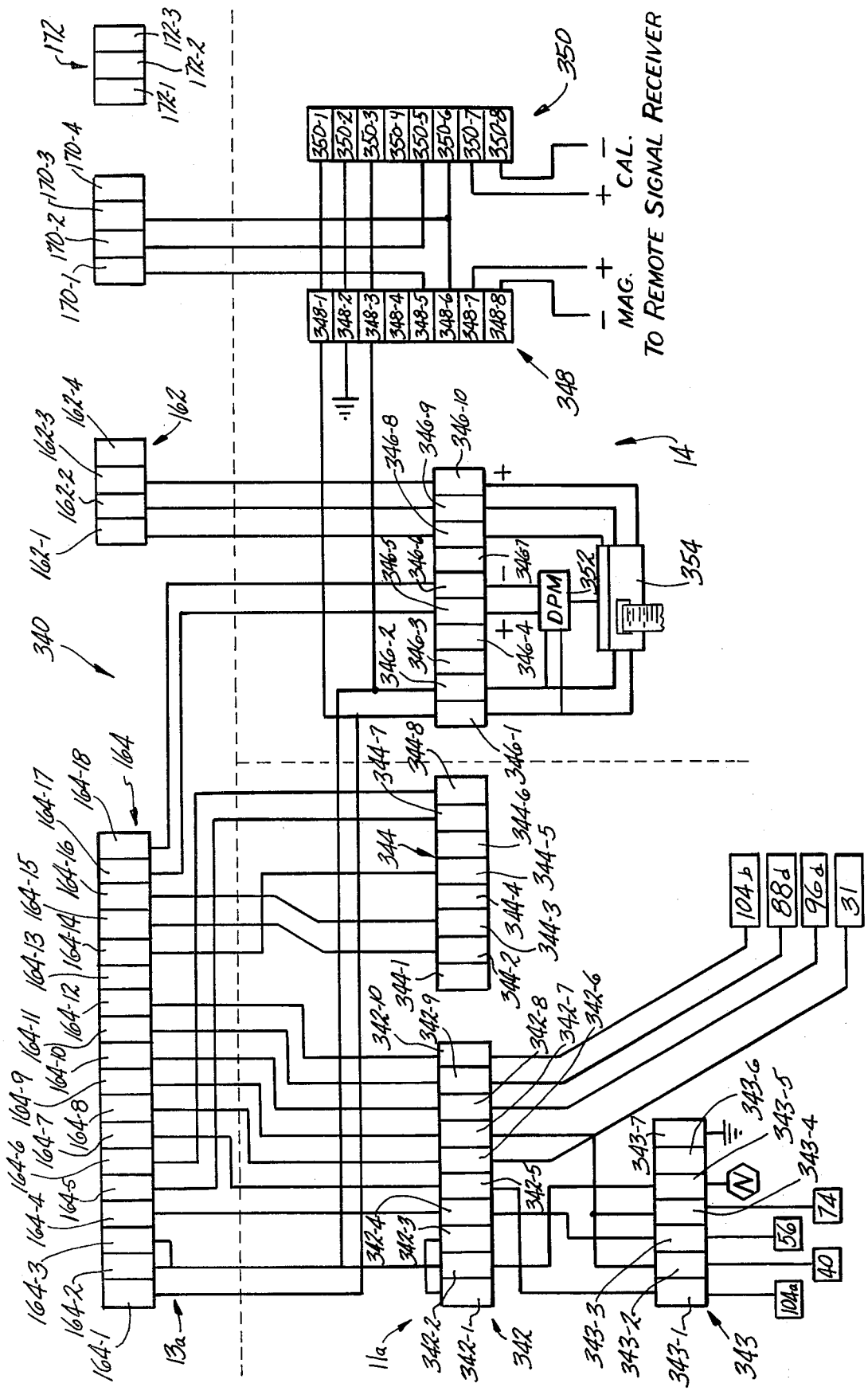

CALCIUM MAGNESIUM ANALYZER

This invention relates to an analytical, chemical method and apparatus therefor and particularly to an analytical, chemical instrument for monitoring extremely low magnesium and calcium concentrations in solutions such as electrolyte feed streams to electrolytic cells.

Diaphragm and membrane type electrolytic cells for electrolysis of alkali metal halides to produce alkali metal hydroxides (e.g., caustic soda or caustic potash), halogens (e.g. chlorine) and hydrogen are in use and are being refined and developed by the chemical industry. The diaphragms and membranes currently utilized in such diaphragm and membrane cells have been found to operate most efficiently when used with cells having electrolyte feed streams with extremely low concentrations of calcium and magnesium, preferably under 5 parts per million by mass. There is, therefore, a need for a means of monitoring the calcium and magnesium concentrations in the electrolyte feed streams.

One traditional method of chemical analysis for low level calcium and magnesium is by titration of a sample with EDTA until a given color change is achieved with the calcium-magnesium concentration being calculated from the amount of EDTA required to produce the color change. The other traditional method is atomic absorption analysis of the sample. The atomic absorption method has been found to be unsatisfactory for use with many electrolytic feed streams because of high sodium background indications which "mask" the indication caused by such minute quantities of calcium.

The titration method has been found by me to be unsatisfactory because the color change is so small at these extremely low calcium-magnesium levels. Furthermore, the titration and atomic absorption methods are basically laboratory analytical methods requiring sophisticated knowledge, constant attention or numerous calculations. There is a need for an analytical instrument which is sufficiently automated or simplified so that it can be more readily and more reliably utilized by production personnel in monitoring extremely low concentrations of calcium and magnesium, particularly in electrolytic cells.

A semi-automatic colorimetric laboratory analytical method is known in which two separate colorimetric absorption analyses are run at a wavelength of 680 mu on separate brine samples from an electrolytic cell brine feed stream. The first analysis is automatically run using Calmagite (1-[1-hydroxyl-4-methyl-2-phenylazo]-2-napthol-4-sulfonic acid) as an indicator reagent and KCN (potassium cyanide), TEA (triethanolamine) and ascorbic acid as masking reagents and distilled water as solvent. A second analysis is then automatically made on a second sample substituting an aqueous magnesium-EDTA (ethylenedinitrilotetraacetic acid) solution for the distilled water. The first analysis produces a % transmission recording which is then manually correlated with a calibration table to achieve an indication of the magnesium in the first sample. The second analysis produces a % transmission recording which is then manually correlated with a calibration table to achieve an indication of the amount of calcium plus magnesium in the second sample. The concentration of magnesium in the first sample is then subtracted from the concentration of Ca+Mg in the second sample to indicate the concentration of calcium in the second sample in excess of the concentration of magnesium in the first sample. If magnesium concentration differs from the first to the second sample, an erroneous indication of calcium concentration will occur. Also, laborious manual calibrations are required which make the method too complicated for reliable use by unsophisticated production personnel. Furthermore, the analyzer of the above colorimetric method is subject to error because distilled water or aqueous MgEDTA solution are introduced through a single tube.

These and other problems are solved by the method of the present invention which provides a method of monitoring calcium and magnesium mass concentrations of less than about 500 parts per million of solution in a liquid stream which comprises:

(a) automatically trapping a single fixed volume of liquid from said liquid stream in a sample chamber;

(b) automatically colorimetrically analyzing said single trapped sample to provide separate indications of the magnesium and calcium concentrations in said sample;

(c) automatically recording said separate indications, and (d) automatically repeating said trapping, analyzing and recording sequence at predetermined time intervals so as to intermittently monitor said calcium and magnesium concentration levels in said liquid stream.

Another method of the present invention solves these and other problems by providing a method of monitoring calcium and magnesium mass concentrations of less than about 500 parts per million parts of solution in a liquid stream which comprises:

(a) supplying a first predetermined quantity of liquid from said liquid stream to a sample chamber;

(b) adding a predetermined quantity of a colorimetric reactant to said sample chamber so as to produce a first colorimetric reaction with magnesium ions in said first quantity of liquid;

(c) measuring change of color due to said first colorimetric reaction so as to provide an indication of the magnesium concentration in said stream;

(d) adding a predetermined quantity of Ca-Mg substitute to increase the magnesium concentration in said first quantity of liquid by an amount directly proportional to the concentration of calcium in said first quantity of liquid to create an additional colorimetric reaction with said added colorimetric reactant; and (e) measuring additional change of color due to said second colorimetric reaction so as to provide an indication of the calcium concentration in said liquid stream.

The invention is more fully described in the following drawings in which:

FIG. 5 is a schematic diagram of the electrical amplification and auto-zero circuit of FIG. 3; and FIG. 6 is a schematic diagram showing the electrical wiring interconnecting the control section of FIG. 3 with the various elements of the analyzer of FIGS. 1 and 2.

Figure 1:
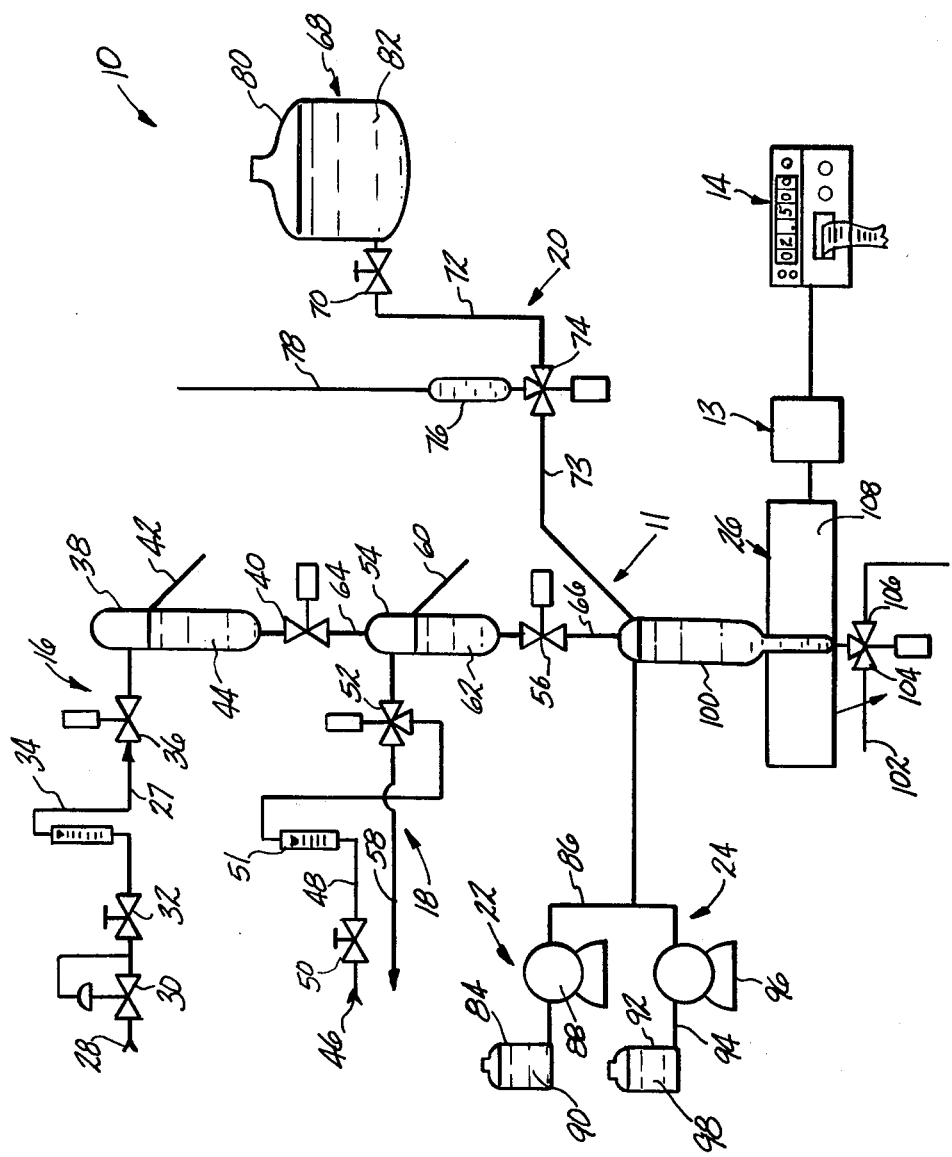
FIG. 1 is a schematic flow diagram of a first preferred calcium-magnesium analyzer embodying the invention.

FIG. 1 is a schematic flow diagram of a preferred calcium-magnesium analyzer 10 embodying the invention. Analyzer 10 comprises a sampling-reagents dispensing means 11, a photometric detector means 26, an electronic control means 13 and a display means 14.

Dispensing means 11 comprises a fixed volume solvent supply means 16, a fixed volume sample supply means 18, a fixed volume indicator supply means 20, a fixed volume masking agent supply means 22 and a fixed volume calcium-magnesium substitute supply means 24. A mixing means 102 can be added to dispensing means 11 or photometric detector means 26, if desired.

Solvent supply means 16 preferably comprises a conduit 27, a connector means 28, a constant pressure outlet regulating valve 30, a throttle valve 32, a flowmeter 34, a first normally closed solenoid shut off valve 36, a fixed volume solvent storage means 38 and a second normally closed solenoid shut off valve 40, although valves 30 and 32 and flowmeter 34 may be deleted where a constant pressure regulated flow solvent source is available. Connector means 28 is adapted for connection to a source of solvent and valves 30 and 32 serve to provide a selected regulated constant volume flow rate to storage means 38 when valve 36 is open. Storage means 38 is preferably provided with a fixed volume limiting device such as a drain 42 so that storage means 38 can isolate and store a fixed volume of solvent 44, such as for example distilled water, therein to be supplied to photometric detector means 26 upon selective opening of valve 40. Solvent supply means 16 can be connected in series or parallel with supply means 18, 20 or 22 to photometric detector means 26. Any other fixed volume supply means can be substituted for means 16 so long as automatic control thereof is possible. Supply means 16 is preferably constructed of materials which will not generate or absorb calcium or magnesium to or from solvent 44 so that accurate calcium and magnesium analysis is not hindered. For example, conduit 27 could be polyethylene or tetrafluoroethylene, valves 30, 32, 36 and 40 could be lined with tetrafluoroethylene and flowmeter 34 and storage means 38 could be glass.

Sample supply means 18 comprises sample connector means 46, sample supply conduit 48, throttle valve 50, flowmeter 51, third solenoid shut off valve 52, fixed volume sample storage means 54, fourth solenoid shut off valve 56 and sample outlet conduit 58. Connector means 46 is adapted to be connected to a source of sample fluid, such as for example a brine feed stream for an electrolytic cell. Conduit 48 serves to feed fluid from connector means 46 to sample storage means 54 when solenoid valve 52 is selectively open. Throttle valve 50 is placed within conduit 48 between connector means 46 and solenoid valve 52 in order to regulate the flow rate of sample through solenoid valve 52 when solenoid valve 52 is open and thus regulates the time required to fill sample storage means 54. Flowmeter 51 gives a visual indication of the flow rate selected by adjustment of throttle valve 50. Solenoid valve 52 is a three-way valve having a normally open flow path from storage means 54 to sample outlet conduit 58 and a normally closed flow path from sample supply conduit 48 to sample storage means 54. Solenoid valve 52 is selectively opened in response to a signal generated by electronic control means 13 to allow sample storage means 54 to be filled with a sample fluid 62. Sample storage means 54 is provided with a fixed volume limiting device such as a drain 60 so that storage means 54 can isolate and store a fixed volume of sample 62, such as for example liquid brine from an electrolyte feed stream of an electrolytic cell, therein to be supplied to photometric detector means 26 upon selective opening of valve 56. Sample supply means 18 can be connected in series or parallel with supply means 16, 20 or 22 to photometric detector means 26. Any other fixed volume supply means can be substituted for means 18 so long as automatic control thereof is possible. Supply means 18 is preferably constructed of materials which will not generate or absorb calcium or magnesium to or from sample 62 so that accurate calcium and magnesium analysis is not hindered. For example, conduits 48 and 58 could be polyethylene or tetrafluoroethylene, connector means 46 and valves 50, 52 and 56 could be lined with tetrafluoroethylene and flowmeter 51 and storage means 54 could be glass.

Indicator supply means 20 comprises indicator supply 68, throttle valve 70, first indicator conduit 72, second indicator conduit 73, fifth solenoid valve 74, fixed volume indicator storage means 76 and vent 78. Indicator supply 68 is preferably a bottle or tank 80 containing a sufficient quantity of indicator reagent 82 for prolonged periods of operation of calcium-magnesium analyzer 10. Conduit 72 supplies indicator reagent 82 from supply 68 through valves 70 and 74 to fixed volume indicator storage means 76 when solenoid valve 74 is in its normal position. Throttle valve 70 serves to selectively regulate the flow rate through conduit 72 when valve 74 is in its normal position. Valve 74 is normally open to flow from conduit 72 to storage means 76 and is selectively closed to flow from conduit 72 to storage means 76. When solenoid valve 74 is closed to flow from conduit 72 to storage means 76, valve 74 is simultaneously open to flow through conduit 73 from storage means 76 to photometric detector means 26 to thereby supply a predetermined fixed volume of indicator reagent 82 to photometric detector means 26. Indicator supply means 20 can be connected in series or parallel with supply means 16, 18 or 22 to photometric detector means 26. Any other fixed volume supply means can be substituted for supply means 20 so long as automatic control thereof is possible. Supply means 20 is preferably constructed of materials which will not generate or absorb calcium or magnesium to or from indicator reagent 82 so that accurate calcium and magnesium analysis is not hindered. For example, conduits 72 and 73 could be polyethylene or tetrafluoroethylene tubing, valves 70 and 74 could be lined with tetrafluoroethylene and tank 80 and storage means 76 could be glass. Vent 78 serves to allow for escape of air from photometric detector means 26 in order to reduce the amount of foam or froth due to the preferred air mixing of the contents of photometric detector means 26.

Masking agent supply means 22 comprises masking agent supply 84, conduit 86 and a dispenser 88. Dispenser 88 serves to dispense a fixed volume of masking agent 90 from masking agent supply 84 through conduit 86 to photometric detector means 26. Masking agent supply 84 can be simply an inverted bottle of masking agent 90 connected directly to conduit 86 or any other suitable source of masking agent 90. Dispenser 88 can be a simple remotely controllable plunger-pump type fluid injector or other small volume fluid injector adapted for automatic remotely controlled operation or can be a supply means constructed substantially in the manner shown for either supply means 16, 18 or 20 so long as a fixed volume of masking agent is provided to photometric detector means 26. Masking agent supply means 22 can be connected in series or parallel with supply means 16, 18 or 20 to photometric detector means 26. Supply means 22 is preferably constructed of materials which will not generate or absorb calcium or magnesium to or from solvent 44 so that accurate calcium and magnesium analysis is not hindered. For example, supply means 20 could be constructed of the same materials as noted above for supply 16, 18 and 20.

Ca-Mg (calcium-magnesium) substitute supply means 24 comprises Ca-Mg substitute supply 92, conduit 94 and fixed volume Ca-Mg substitute dispenser 96. Dispenser 96 serves to dispense a fixed volume of a Ca-Mg substitute 98, such as for example MgEDTA, from supply 92 through conduit 94 to photometric detector means 26. Conduit 94 can be connected to conduit 86 of masking agent supply means 22, if so desired. Dispenser 96 can be constructed in similar manner to supply means 16, 18, 20 or 22 and hence is not depicted in detail. Supply means 24 is not connected in series with supply means 16, 18, 20 or 22 to photometric detector means 26, but rather is connected in parallel with supply means 16, 18, 20 and 22 to photometric detector means 26 in order that Ca-Mg substitute 98 can be separately provided to photometric detector means 26 at a later time than solvent, sample, indicator and masking agent are supplied to photometric detector means 26 by supply means 16, 18, 20 and 22.

Photometric detector means 26 is connected to supply means 16, 18, 20, 22 and 24 and receives the solvent, sample, indicator, masking agent and Ca-Mg substitute provided respectively thereby. Photometric detector means 26 comprises detector chamber 100, air mixer 102, solenoid valve 104, drain conduit 106 and photometer means 108. Air mixer 102 serves to slowly supply air through detector chamber 100 in order to help mix the contents thereof. Solenoid valve 104 is normally open to flow from air mixer 102 to detector chamber 100 and normally closed to flow from detector chamber 100 to drain conduit 106. Solenoid valve 104 can be selectively closed to flow from air mixer 102 to detector chamber 100 and simultaneously open to flow from detector chamber 100 to drain conduit 106 in order to allow the contents of detector chamber 100 to be emptied following photometric analysis thereof by photometer means 108. Photometer means 108 is connected to electronic control means 13 and provides an output indicative of the concentration of calcium and magnesium present within detector chamber 100 in the manner below described.

Electronic control means 13 controls the sequential operation of solenoid valves 36, 40, 52, 56, 74, 104 and dispensers 88 and 96 in order to fill detector chamber 100 with fixed volumes of solvent, sample, indicator, masking agent and Ca-Mg substitute in the proper timed sequences. Electronic control means 13 also analyzes the output of photometer means 108 and generates an input to display means 14 which input can be displayed by display means 14 to give direct readings of the concentrations of calcium and magnesium in the fixed volume of sample fluid 62 supplied to detector chamber 100 by sample supply means 18. Display means 14 can be any conventional recorder capable of producing such a display. A particularly preferred display means 14 is an LED type digital display means which provides direct numerical readings of the concentrations of calcium and magnesium in parts per million.

Figure 2:
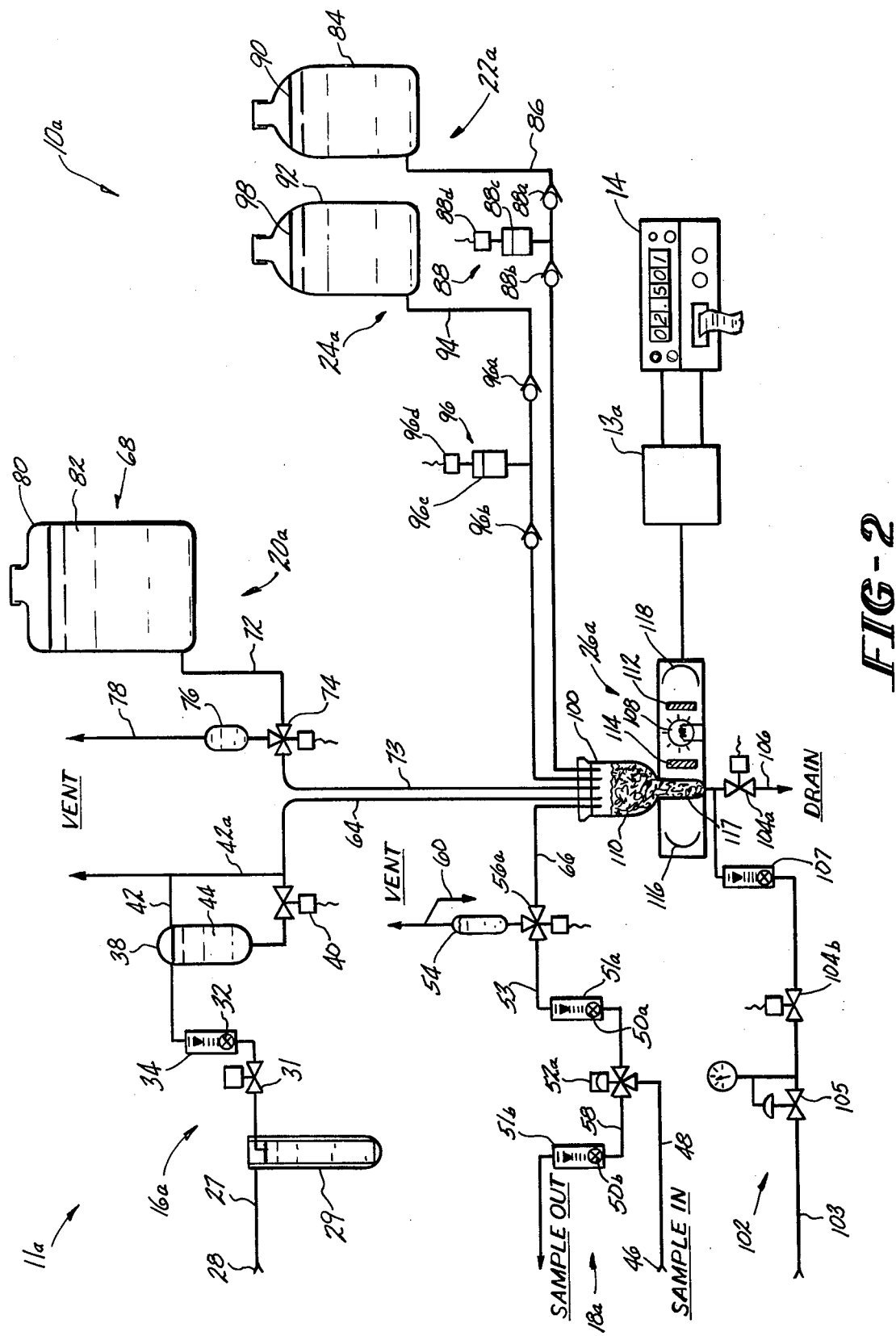
FIG. 2 is a schematic flow diagram of a second preferred Ca-Mg (calcium-magnesium) analyzer embodying the invention.

FIG. 2 is a schematic flow diagram of a second preferred Ca-Mg analyzer 10a embodying the invention. Analyzer 10a, like analyzer 10 of FIG. 1, comprises a sampling-reagents dispensing means 11a, a photometric detector means 26a, an electronic control means 13a and a display means 14.

Dispensing means 11a comprises a fixed volume solvent supply means 16a, a fixed volume sample supply means 18a, a fixed volume indicator supply means 20a, a fixed volume masking agent supply means 22a, a fixed volume Ca-Mg substitute supply means 24a and a mixing means 102.

Solvent supply means 16a is similar to solvent supply means 16 of FIG. 1 except that first normally closed solenoid shut off valve 36 is placed toward connector means 28 from flowmeter 34 and valve 32. Also, pressure outlet regulating valve 30 is omitted, and an ion exchange column 29 has been placed in conduit 27 upstream (towards connector 28) from flowmeter 34 and solenoid valve 36 in order to purify the solvent supply entering analyzer 10a through conduit 27. In particular, ion exchange column 29 is adapted to remove calcium and magnesium from solvent 44 prior to the use of solvent 44 in analyzer 10a. Solvent supply means 16a is different from solvent supply means 16 by the further addition of rinse connector line 42a which places drain 42 in fluid communication with detector chamber 100 in order to automatically rinse detector chamber 100 by draining solvent through detector chamber 100 when solenoid valve 36 is open and storage means 38 is full. Solvent outlet conduit 64 of solvent supply means 16a is directly connected to detector chamber 100 rather than to sample storage means 54 as in analyzer 10 in order to allow the automatic rinse of detector chamber 100. Otherwise, solvent supply means 16a can be constructed in the same manner as solvent supply means 16. Sample supply means 18a is similar to sample supply means 18 except that flowmeter 15 is replaced by sample supply flowmeter 51a placed towards sample storage means 54 from bypass valve 52a and sample bypass flowmeter 51b placed in sample outlet conduit 58. Sample supply flowmeter 51a measures the flow rate to sample storage means 54 while sample bypass flowmeter 51b measures the amount of sample bypassing storage means 54 and returning to the sample source (not numbered). Thus, flowmeter readings occur regardless of whether sample storage means 54 is being filled or sample is being returned to the sample source. This allows sample supply means 18 to be regulated such that a known flow rate can be provided through flowmeter 51a to storage means 54 regardless of the flow rate through sample supply conduit 48 to bypass valve 52a. Any desired flow rate can be provided through flowmeter 51a and sample fill conduit 53 by regulating the proportion of fluid which is allowed to flow through bypass valve 52a into sample fill conduit 53. The remainder of the fluid supplied to bypass valve 52a is returned to the sample source through conduit 58 and flowmeter 51b, and flowmeter 51b indicates the flow rate of this bypassing fluid. Sample storage means 54 of sample supply means 18a is provided with a vent 55 and is not connected to solvent supply means 16a. Otherwise, sample supply means 18a can be identical to sample supply means 18.

Indicator supply means 20a is identical to indicator supply means 20 of FIG. 1 except that optional throttle valve 70 is deleted.

Masking agent supply means 22a can be identical to masking agent supply means 22 of FIG. 1, however, dispenser 88 is shown in detail to include inlet section valve 88a, outlet section 88b, dispenser plunger 88c and electromechanical transducer 88d. Electromechanical transducer 88d is selectively actuated to reciprocate plunger 88c in order to draw masking agent 90 from supply 84 through inlet section valve 88 and dispense masking agent 90 through outlet section valve 88b and conduit 86 to detector chamber 100. Dispenser 88 could be replaced by a bulb-type fixed volume dispenser such as utilized in sample supply means 16a, 18a or 20a, but for extremely small volumes of fluid, it has been found that an injector type dispenser such as shown in FIG. 2 is preferred.

Ca-Mg substitute supply means 24a can be identical to Ca-Mg substitute supply means 24, of FIG. 1, however, dispenser 96 is shown in more detail to comprise inlet check valve 96a, outlet check valve 96b plunger 96c and electromechanical transducer 96d which are operated in similar fashion to that described with respect to dispenser 88 in order to dispense a small fixed volume of Ca-Mg substitute 98 from Ca-Mg substitute supply 22 through conduit 94 to detector chamber 100.

Mixing means 102 can be an air mixing means comprising air supply conduit 103, constant pressure pneumatic regulator valve 105, solenoid powered pneumatic shut-off valve 104b and pneumatic flowmeter 107 in that sequence. Thus air is supplied through conduit 103 to detector chamber 100 is at a constant pressure regulated by pneumatic regulator valve 105 and indicated by pneumatic flowmeter 107 when solenoid shut-off power pneumatic valve 104b is selectively open since conduit 103 is connected directly to detector chamber 100. The introduction of this regulated air stream provides additional mixing of the mixed contents 110 of detector chamber 100 in order to achieve more uniform and accurate photometer readings.

Solenoid valve 104 of analyzer 10 is replaced in analyzer 10a by solenoid valves 104a and 104b. Solenoid valve 104a selectively opens and closes drain conduit 106 while solenoid valve 104b selectively allows and prevents flow of mixing air to detector chamber 100. The separation of valves 104a and 104b provides an added degree of flexiblity to analyzer 10a.

Photometer 26a comprises lamp 108, fillers 112 and 114, measurement receiver 116 and reference receiver 118. A lower portion 117 of detector chamber 100 lies between filler 114 and measurement receiver 116 while the space between filler 112 and reference receiver 118 is void. Thus the signals received by measurement receiver 116 and reference receiver 118 can be compared and a differential signal produced indicative of the effect of lower portion 117 upon the signal received by measurement receiver 116. This differentiation is accomplished by the circuitry of control section 13a described below.

Figure 3:
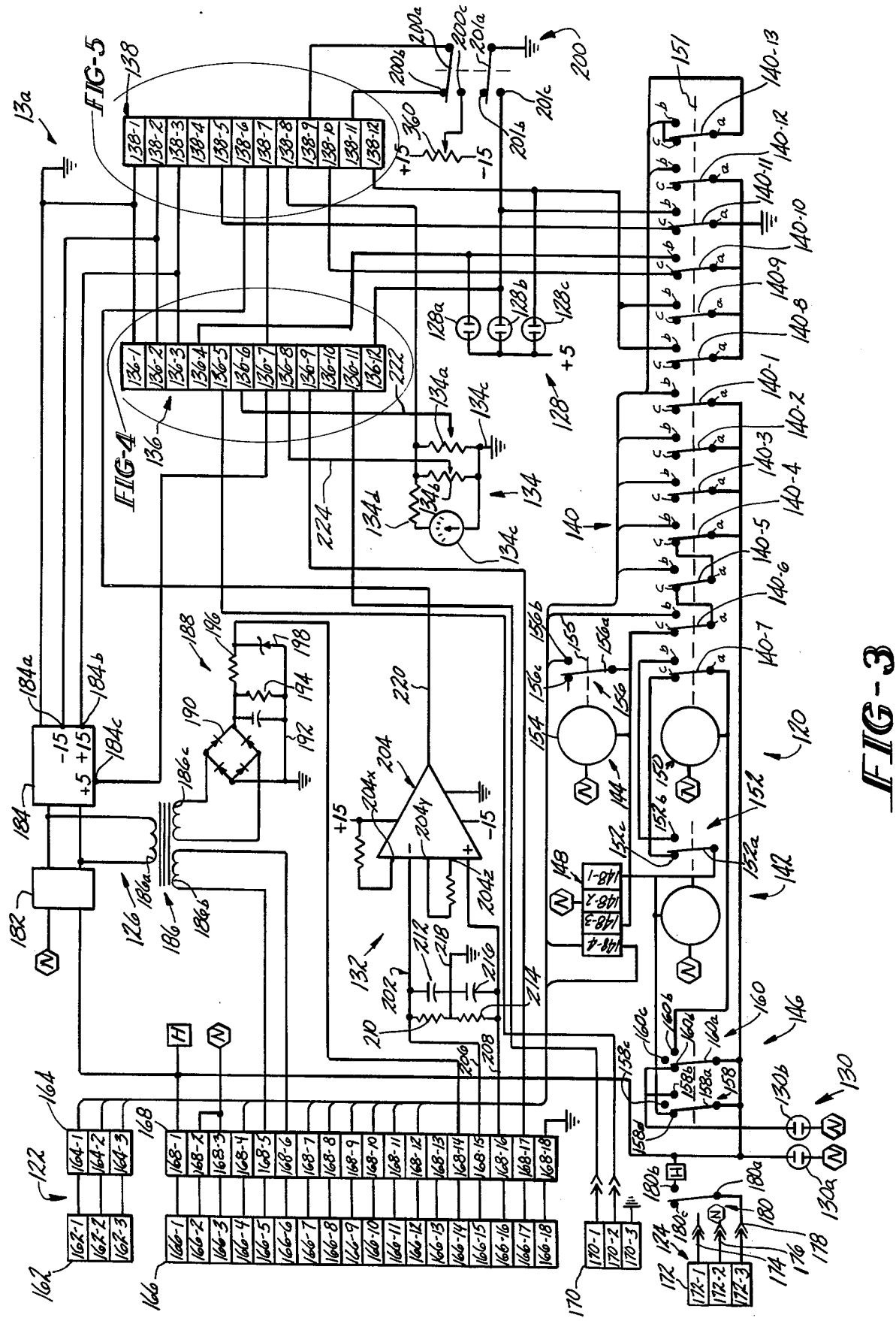
FIG. 3 is a schematic circuit diagram of a control section of the analyzer of FIGS. 1 and 2.

FIG. 3 is a schematic diagram of electrical control section 13a. It will be understood by skilled artisans that a similar electrical circuit could be utilized for control section 13. Control section 13a comprises timer section 120, terminal section 122, AC power section 124, DC power section 126, indicator light sections 128 and 130, input amplifier section 132, calibration section 134, holding and switching circuit section 136 and auto-zero and compensation circuit section 138.

Timer section 120 comprises multiple cam switch portion 140, frequency timer 142, air duration timer 144, timer select switch 146 and an optional terminal 148. Multiple cam switch portion 140 further comprises 13 cam switches 140-1 through 140-13 and an electrical drive unit 150. Switches 140-1 through 140-13 each have a cam-operated mechanical contactor "a" and two terminals "b" and "c". Each contactor "a" is selectively connected to either its respective terminal "b" or its respective terminal "c". Switches 140-1 through 140-7 control the operation of the various solenoid valves and injectors above noted and are operable to close or open AC circuits. Switches 140-8 through 140-13 are ground contact switches adapted to selectively ground certain portions of circuit sections 136 and 138. Electrical drive unit 150 serves to rotate a shaft 151 to which 13 cams are attached so as to rotate with rotation of shaft 151. Electrical drive unit 150 is turned off and on by either manipulation of timer select switch 146 or operation of frequency timer 142 and preferably operates with a frequency of 4–10 minutes per revolution of shaft 151 so as to perform a complete Ca-Mg analysis each 4–10 minutes during the time that electrical drive unit 150 is in operation. Switches 140-1 through 140-13 control the following specific operations listed in the Table below:

| MULTICAM SWITCH OPERATIONS | |
| --- | --- |
| SWITCH NUMBER | OPERATION CONTROLLED |
| 140-1 | sample drain |
| 140-2 | rinse water |
| 140-3 | reagent, water |
| 140-4 | masking agent dispense |
| 140-5 | Ca-Mg sub. dispense |
| 140-6 | sample add |
| 140-7 | timer interrupter |
| 140-8 | auto-zero activate |
| 140-9 | auto-zero activate |
| 140-10 | Ca read or dilution compensation |
| 140-11 | Mg read or dilution compensation |
| 140-12 | print cr off |
| 140-13 | printer |

As shown in FIG. 3, the left position of contactors "a" places contactors "a" in contact with their respective terminals "c", while movement of contactors "a" to the right places contactors "a" in contact with their respective terminals "b". Movement of contactors "a" occurs independently for each switch 140-1 through 140-13. The operation of switches 140-1 through 140-13 will be described in greater detail below in connection with the operation of analyzers 10 and 10a.

Frequency timer 142 is selectively connected and disconnected from an AC power source by manipulation of timer select switch 146. When frequency timer 142 is connected to such AC power source, frequency timer 142 operates a single cam switch 152 to selectively place a contactor 152a in contact with either a first terminal 152b or a second terminal 152c. Terminal 152b is directly connected to terminal 140-7b (terminal "b" of switch 140-7) and terminal 152c is directly connected to terminal 140-7c (terminal "c" of switch 140-7). Terminal 152c is the off position for switch 152 and provides power to electrical drive unit 150 only when contactor 140-7a (contactor "a" of switch 140-7) is in contact with terminal 140-7c, which is the reset position of switch 140-7. Electrical drive unit 150 will rotate shaft 151 until such time as contactor 140-7a is forced by the cam associated with switch 140-7 to move from contact with "reset" terminal 140-7c into contact with a "ready" terminal 140-7b at which time electrical drive unit 150 will be disconnected from its AC power source until such time as contactor 152a moves from contact with "off" terminal 152c into contact with "on" terminal 152b. When contactor 152a is in contact with terminal 152b and contactor 140-7a is in contact with terminal 140-7b, electrical drive unit 150 is once again connected to its AC power source and the Ca-Mg analysis sequence continues to completion at which time contactor 140-7a moves from terminal 140-7b back to terminal 140-7c thus disconnecting electrical drive unit 150 from its AC power source. When contactor 152a is returned by operation of its associated cam from terminal 152b to terminal 152c, electrical drive unit 150 is again connected to its AC power source and allowed to once again return or "reset" to the start of a cycle at which time contactor 140-7a moves from timer 140-7c to terminal 140-7b and the sequence begins again.

Air duration timer 144 comprises electrical motor 154, a shaft 155 and a switch 156. A cam is attached to shaft 155 and serves to automatically operate switch 156. Switch 156 has a contactor 156a and two terminals 156b and 156c. When contactors 140-4a, 140-5a and 140-6a are all in their "off" position in contact with their respective terminals 140-4c, 140-5c and 140-6c, electrical motor 154 is connected to its AC power source, motor 154 rotates shaft 155 and its associated cam until such time as one of contactors 140-4a, 140-5a and 140-6a moves out of contact with its associated terminal 140-4c, 140-5c or 140-6c at which time motor 14 is disconnected from its AC power source and motor 154 therefore ceases to rotate shaft 155. Contactor 156a is normally in contact with terminal 156b so that AC power is provided to solenoid valve 104b when contactors 140-4a, 140-5a and 140-6a are in contact with their respective terminal 140-4c, 140-5c and 140-6c. Electrical motor 154 serves to time the duration of AC power to solenoid valve 104b by timing how long contactor 156a remains in contact with terminal 156b. After a predetermined time, preferably about 15 seconds, contactor 156a is moved by its associated cam from terminal 156b to terminal 156c. Terminal 156c is a "dead" terminal so that the AC power source is disconnected from solenoid valve 104b by such movement. Contactor 156a remains in contact with terminal 156c until a change occurs in the position of contactor 140-4a, 140-5a or 140-6a such that contactor 140-4a, 140-5a or 140-6a moves into contact with its associated terminal 140-4b, 140-5b, or 140-6b and then returns to contact with its respective terminal 140-4c, 140-5c or 140-6c to reclose the series connection from the AC power source through terminals 140-4c, 140-5c and 140-6c to electrical motor 154.

Timer select switch 146 is a double-pole, three-position manual contact switch and comprises connected switches 158 and 160. Switch 158 has a contactor 158a and three terminals 158b, 158c and 158d and switch 160 has a contactor 160a and three terminals 160b, 160c and 160d. Contactors 158a and 160a are connected in parallel to the first wire of a two-wire AC power source. Terminals 158b and 160d are conneced through indicator light section 130 to the second wire of the AC power source. Terminals 158c and 160c are dead terminals. Terminal 158d is connected through frequency timer 142 to the second wire of the AC power source. Terminal 160b is connected through electrical drive unit 150 to the second wire of the AC power source. When contactor 158a is in contact with one of terminals 158b, 158c and 158d, contactors 160a is in contact with terminal 160b, 160c or 160d, respectively. Thus, when contactor 150a is in contact with terminal 158b so as to produce an indication on indicator light section 130, contactor 160a is in contact with terminal 160b to provide continuous power to electrical drive unit 150 so as to bypass frequency timer 142 and provide continuous operation of electrical drive unit 150 and thereby provide for continuous Ca-Mg analyses. When contactor 158a is in its off position in contact with terminal 158c, contactor 160a is also in its off position in contact with terminal 160c. When contactor 158a is in contact with terminal 158d to provide continuous power to frequency timer 142 so as to provide intermittent power to electrical drive unit 150 to thereby provide for intermittent Ca-Mg analyses at a frequency determined by frequency timer 142, contactor 160a is in contact with terminal 160d to provide an indication on indicator light section 130.

Optional terminal 148 provides for connection of a wire from terminal section 122 to terminal 156b and also provides for connection of terminal 140-6c and terminal 158d to external devices (not shown).

Terminal section 122 comprises five sets of terminals 162, 164, 166, 168 and 170. Terminal sets 162, 166 and 170 are connected to various portions of analyzer 10 in the manner described below. Terminal sets 162 and 166 are directed connected to terminal sets 164 and 168, respectively. Terminal sets 164 and 166 are in turn connected to various components of control section 13a in the manner described below. Terminal set 162 comprises three terminals 162-1, 162-2 and 162-3. Terminal set 164 comprises three terminals 164-1, 164-2 and 164-3 which are respectively connected to terminals 162-1, 162-2 and 162-3. Terminal set 166 comprises 18 terminals 166-1 through 166-18 and terminal set 168 comprises 18 corresponding terminals 168-1 through 168-18 which are respectively connected to terminals 166-1 through 166-18.

Terminal 164-1 is connected to contactor 140-13a. Terminal 164-2 is connected to terminals 140-13b and 140-13c. Terminal 164-3 is connected to terminal 140-12b. Terminal 168-1 is connected to a first wire of an external two-wire AC power source, such as for example normal 115 volt household current. Terminals 168-2 and 168-3 are connected to the second wire of the external AC power source. Specifically, this connection is made through AC power section 124 as described below. Terminal 168-4 is connected to terminal 140-6b. Terminal 168-5 is connected through DC power section 126 to terminal 168-6. Terminal 168-7 is connected to terminal 140-1b. Terminal 168-8 is connected to terminal 140-2b. Terminal 168-9 is connected to terminal 140-3b. Terminal 168-10 is connected to terminal 140-4b. Terminal 168-11 is connected to terminal 140-5b. Terminal 168-12 is connected to optional terminal 148. Terminal 168-13 is blank or "dead" to serve as a spacer or insulator between terminals 168-1 through 168-12, which preferably carry 115 volt AC current and terminals 168-14 through 168-18 which preferably carry photometer measurement signals. This spacing serves to reduce noise in the photometer signal due to noise in the 115 volt AC current. Terminal 168-14 is connected to DC power section 126. Terminal 168-15 is connected to the inverting input of the summing amplifier of input amplifier section 132. Terminal 168-16 is connected to the non-inverting input terminal of the summing amplifier of input amplifier section 132. Terminal 168-17 is connected to holding and switching circuit section 136 in a manner described below. Terminal 168-18 is connected to ground. Terminals 170-1 and 170-2 are connected to holding and switching circuit section 136 in a manner described below. Terminal 170-3 is connected to ground.

AC power section 124 serves as the source of AC power for analyzer 10a and comprises terminal set 172, circuit breakers 174, 176 and 178 and main power switch 180. Terminal set 172 comprises three terminals 172-1, 172-2 and 172-3 which are respectfully connected to the ground, neutral and hot lines of a three-wire external 115 volt AC power source such as normal household current. Terminals 172-1, 172-2 and 172-3 are also respectively connected to circuit breakers 174, 176 and 178 to prevent overload of the electrical circuit of analyzer 10a. Any other suitable overload protection device, such as for example fuses, could be substituted for circuit breakers 174, 176 and 178. Main power switch 180 comprises a contactor 180a and two terminals 180b and 180c. Terminal 180b is connected to terminal 168-1 and indicator light section 130. Terminal 180c is a "dead" terminal. Thus, main power switch 180 can be manually or automatically operated to turn analyzer 10a on or off and an indication is provided on indicator light section 130 when analyzer 10a is turned on.

DC power section 126 comprises AC noise suppression filter 182, AC to DC power converter 184, AC transformer 186 and full wave rectifier circuit 188. AC noise suppression filter 182 serves to minimize voltage fluctuations or "noise" in the input to DC power converter 184 and AC transformer 186 to thereby reduce noise in the DC outputs from converter 184 and transformer 186. Filter 182 is connected to terminal 180b and terminals 168-2 and 168-3. Filter 182 is also connected to the AC input terminals (not numbered) of DC power converter 184 and to the AC input terminals of AC transformer 186. DC power converter 184 serves to convert the 115 volt AC electrical supply from filter 182 into three DC voltages outputs 184a, 184b and 184c. Output 184 is −15 volts DC. Output 184b is +15 volts DC. Output 184c is +5 volts DC. Outputs 184a and 184b are connected to amplifiers within circuit sections 136 and 138 as described below. Output 184c is connected to relays within circuit sections 136 and 138 as described below. Transformer 186 comprises one input coil 186a and two output coils 186b and 186c. Coil 186a receives the 115 volt AC output from filter 182 and transformer 186 transforms that 115 volt AC signal into a 6.3 volt AC output signal in coil 186b and a 125 volt AC output signal in coil 186c. Coil 186b is connected to terminals 168-5 and 168-6 to supply 6.3 volt AC current to a lamp within photometric detector means 26a. Coil 186c is connected through rectifier circuit 188 to terminal 168-14 to provide a +90 volt DC charge to the anodes or receivers 116 and 118 of photometric detector means 26a to draw photons from lamp 108 toward receivers 116 and 118. Full wave rectifier circuit 188 comprises a rectifier grid 190 which is grounded at one terminal and connected in parallel to a capacitor 192 and two separate resistors 194 and 196. Capacitor 192 and resistor 194 are connected through a Zener Diode 198 to terminal 168-14 while resistor 196 is connected directly to terminal 168-14. This circuit arrangement provides a +90 volt DC charge to terminal 168-14 when capacitor 192 is 80 microfarads, resistor 194 is 1,000 ohms and resistor 196 is 33,000 ohms. Any other suitable full wave rectifier circuit could be substituted for circuit 188 so long as a suitable positive DC charge is generated for application to receivers 116 and 118.

Indicator light section 128 comprises three indicator lights 128a, 128b and 128c, each connected in parallel to a +5 volt DC voltage supply such as output 184c. Indicator light 128a is also connected to terminal 140-10b and to circuit section 136 (see FIG. 4) to provide an indication when a calcium concentration reading is being taken by analyzer 10a. Indicator light 128b is connected to terminal 140-11b and to circuit section 136 (see FIG. 4) and also connected to auto-zero switch section 200 as described below, to provide an indication when a magnesium reading is being taken by analyzer 10a. Indicator light 128c is also connected to terminal 140-8b and circuit section 138 (see FIG. 5) to provide an indication when analyzer 10a is being automatically zeroed.

Indicator light section 130 comprises a power indicator light 130a and a timer indicator light 130b. Power indicator light 130a is connected to terminal 180b and to circuit breaker 176 and provides a visual indication when main power switch 180 is closed and power is being provided to analyzer 10a. Timer indicator light 130b is connected to circuit breaker 176 and to terminals 158b and 160d to provide a visual indication when power is being supplied to either frequency timer 142 or electrical drive unit 150.

Input amplifier section 132 comprises filter section 202 and amplifier 204. Filter section 202 has two input wires 206 and 208 connected respectively to terminals 168-15 and 168-16 to receive the signals from receivers 118 and 116, respectively. Wire 206 is connected to ground in parallel through a 50,000 ohm resistor 210 and a 0.1 microfarad capacitor 212. Wire 208 is connected to ground in parallel through a 50,000 ohm resistor 214 and a 0.1 microfarad capacitor 216. Filter section 202 thus comprises wires 206 and 208, resistors 210 and 214, capacitor 212 and 216 and a ground connection 218. Wire 206 is connected to the inverting input of amplifier 204 and wire 208 is connected to the noninverting input of amplifier 204. Amplifier 204 has a +15 volt DC terminal, a −15 volt DC terminal, a ground terminal and three cam terminals 204x, 204y and 204z. The +15 volt DC terminal is connected to cam terminal 204x through a 22,000 ohm resistor and cam terminal 204y is connected to cam terminal 204z through a 5,000 ohm resistor. Amplifier 204 is so constructed that this results in a 20 to 1 amplification of the differential between wires 206 and 208 with the amplified differential output signal being transmitted through an output wire 220 to an input terminal of circuit section 138 as described below. Any other input amplification system can be substituted for amplifier section 132 so long as a suitably amplified differential signal is generated from the signals transmitted to wires 206 and 208 and such differential amplified signal is transmitted to circuit section 138.

Calibration section 134 comprises calcium calibration potentiometer 134a, magnesium calibration potentiometer 134b, indicator 134c and a load resistor 134d. Potentiometers 134a and 134b are connected in parallel to an output terminal of circuit section 138 and in parallel to a ground connection 134e. Potentiometers 134a and 134b are also connected in parallel to indicator 134c and load resistor 134d. Potentiometers 134a and 134b have an output connected through wires 222 and 224, respectively, to Mg and Ca input signal terminals of circuit section 136. Calibration section 134 serves to adjust the span of the output calcium and magnesium signals to produce a properly calibrated reading.

Figure 4:
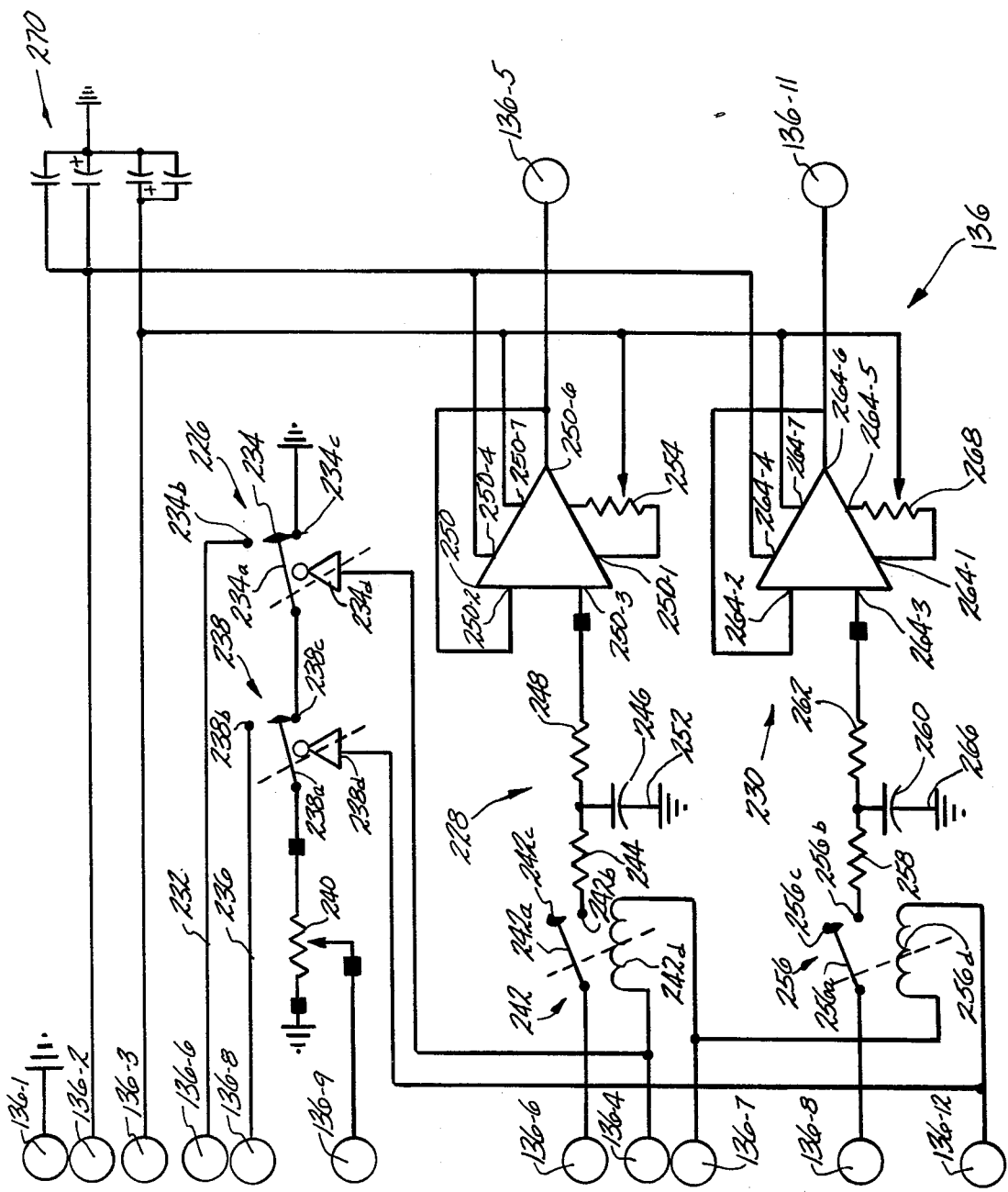
FIG. 4 is a schematic diagram of the electrical holding and switching circuit of FIG. 3.

Referring now to FIG. 4, which shows a schematic diagram of the holding and switching circuit 136 of FIG. 3, it is seen that holding and switching circuit 136 comprises switching section 226, calcium signal holding section 228 and magnesium signal holding section 230. Switching section 226 comprises a calcium input wire 232 connected to a relay switch 234. Switch 234 has contactor 234a, two terminals 234b and 234c and a relay coil 234d. Terminal 234b is connected to wire 232 and terminal 234c is connected to ground. Thus when contactor 234a is moved from its normal position in contact with terminal 234c to a position in contact with terminal 234b, the calcium input signal carried by wire 232 is transmitted to contactor 234a. When relay coil 234d is inactivated, contactor 234a returns to terminal 234c to short-out the calcium input signal. Switching section 226 also includes a magnesium input wire 236 and a second switch 238. Switch 238 has a contactor 238a, two terminals 238b and 238c and a relay coil 238d. When contactor 238a is moved from its normal position in contact with terminal 238c into contact with terminal 238b, the magnesium input signal from wire 236 is transmitted through contactor 238a to a digital panel meter ("DPM") described below, so that a magnesium concentration reading is produced on the DPM. When relay coil 238d is inactivated, contactor 238a returns to terminal 238c which is connected to contactor 234a. When contactors 238a and 234a are both in their normal positions in contact with terminals 238c and 234c, respectively, the DPM is grounded. When contactor 234a is in contact with terminal 234b and contactor 238a is in contact with terminal 238c, the calcium input signal from wire 232 is transmitted through terminal 234b, contactor 234a, terminal 238c and contactor 238a to the DPM. Switching circuit 226 can also include a span potentiometer 240, such as for example a 10,000 ohm potentiometer to allow for adjustment of the scale of readings on the DPM so as to calibrate the voltage of the calcium and magnesium input signals to the voltage necessary to produce a corresponding reading on the DPM. Relay 234d is connected through calcium signal holding section 228 to terminal 140-10b so that when contactor 140-10a moves into contact with terminal 140-10b, relay 234d is activated to move contactor 234a into contact with terminal 234b to generate a calcium concentration reading. Relay 238d is connected through magnesium signal holding section 230 to terminal 140-11b so that when contactor 140-11a is moved into contact with terminal 140-11b, relay 238d is activated to move contactor 238a into contact with terminal 238b to generate a magnesium concentration reading on the DPM.

Calcium signal holding section 228 comprises a relay switch 242, resistor 244, signal storage condenser 246, resistor 248, summing amplifier 250 and a ground connection 252. Relay switch 242 comprises a contactor 242a, terminals 242b and 242c and relay 242d. Contactor 242a is connected to wire 224 as is wire 232 so that the calcium input signal from potentiometer 134a is continuously fed to contactor 242a. Terminal 242b is connected to resistor 244 and terminal 242c is a dead terminal so that when contactor 242a is moved by relay 242d from its normal position in contact with terminal 242c, into contact with terminal 242b, the calcium input signal is transmitted to resistor 244. Relay 242d is connected to output 184c and to terminal 140-10b so that when contactor 140-10a is moved into contact with terminal 140-10b, the calcium input signal from wire 244 is fed to resistor 244. Resistor 244 is connected in parallel to ground connection 252 through condenser 246 and to the non-inverting input 250-3 of amplifier 250 through resistor 248. Resistor 244 is preferably a 10,000 ohm load resistor and resistor 248 is preferably 1,000,000 ohms. Condenser 246 is preferably 5.6 microfarads. Amplifier 250 is preferably an Analog Devices, Inc. Model AD540 amplifier which has seven terminals 250-1 through 250-7. Terminals 250-1 and 250-5 are zero adjusting terminals which are adjusted by manipulation of a potentiometer 254 to supply a given positive DC voltage to terminals 250-1 and 250-5. Terminal 250-2 is the inverting input. Terminal 250-3 is the non-inverting input, as described above. Terminals 250-4 and 250-7 are the −15 volt DC and +15 volt DC inputs, respectively, to amplifier 250. Amplifier 250 serves to amplify the calcium input signal from potentiometer 134a and generate an amplified calcium output signal which is transmitted through output terminal 250-6 to terminal 170-2. This amplified output signal can then be transmitted from terminal 170-2 through suitable transducers to a remote signal receiver, such as for example an alarm system, to indicate when excess calcium is present in the sample being analyzed by analyzer 10a.

Magnesium signal holding section 230 comprises relay switch 256, resistor 258, magnesium signal holding condenser 260, resistor 262 and amplifier 264. Relay switch 256 comprises contactor 256a, terminals 256b and 256c and a relay coil 256d. Contactor 256a is connected to wire 222 as is wire 236. Contactor 256a is normally in contact with terminal 256c and is moved into contact with terminal 256b upon energization of relay coil 256d. Terminal 256b is connected to resistor 258a and terminal 256c is a dead terminal. Relay coil 256d is connected to output 184c and to terminal 140-11b so that when contactor 140-11a is moved into contact with terminal 140-11b, coil 256d is energized and contactor 256a is moved into contact with terminal 256b. When terminal 256b is in contact with terminal 256a, the signal from potentiometer 134b is transmitted to resistor 258. Resistor 258 is in turn connected in series to condenser 260 which is in turn connected to ground connection 266. Resistor 258 is also connected in series through resistor 262 to the inverting input 264-3 of amplifier 264. Resistor 258 is preferably a 10,000 ohm load resistor and resistor 262 is preferably a 1,000,000 ohm resistor. Condenser 260 is preferably a 5.6 microfarad condenser and serves to hold the magnesium signal communicated thereto from resistor 258 upon activation of relay 256d. Amplifier 264 is preferably an Analog Devices, Inc. Model AD540 differential amplifier having seven terminals 264-1 through 264-7. Terminals 264-1 and 264-5 are zero adjusting terminals which are connected through a potentiometer 268 to +15 volt DC output 184b so that potentiometer 268 can be adjusted to apply appropriate voltages to terminals 264-1 and 264-5 to calibrate amplifier 264. Terminal 264-2 is the inverting input of amplifier 264 and is connected to terminal 264-6 which is the output terminal of amplifier 264. Terminal 264-3, as noted above, is the non-inverting input of amplifier 264. Terminals 264-4 and 264-7 are the −15 volt DC and +15 volt DC inputs, respectively, to amplifier 264. Amplifier 264 serves to amplify the signal from potentiometer 134b to generate a continuous magnesium output voltage signal which is transmitted to terminal 170-1. This amplified magnesium signal can be transmitted from terminal 170-1 to a remote signal receiver, such as for example an alarm, to indicate the presence of an excessive concentration of magnesium in the sample being analyzed by analyzer 10a. Circuit section 136 includes a noise suppression circuit 270 which is connected to the −15 volt and +15 volt DC outputs 184a and 184b in order to eliminate voltage fluctuations or "noise" in said outputs. Filter 270 comprises two grounded 47 microfarad capacitors, one connected to each of outputs 184a and 184b, and two 0.01 microfarad grounded capacitors, one connected to each of outputs 184a and 184b in parallel with the 47 microfarad capacitor.

FIG. 5 is a schematic diagram of the auto-zero and compensation circuit section 138 of FIG. 3. Section 138 comprises DC voltage supply portion 272, auto-zero amplification portion 274 and dilution compensation portion 276. DC voltage supply portion 272 comprises ground 278, −15 volt DC supply 280, +15 volt DC supply 282 and noise suppressor 284. Noise suppressor 284 can be identical to noise suppressor 270 and description thereof is thus omitted. Auto-zero amplification portion 274 comprises relay switch 286, resistor 288, auto-zero signal storage condenser 290, resistor 292, amplifier 294, ground 296, resistor 298, resistor 300, and amplifier 302. Relay switch 286 comprises a contactor 286a, two terminals 286b and 286c and a relay coil 286d. Contactor 286a is connected to the output of amplifier 204 through wire 220. Terminal 286b is connected to resistor 288 and terminal 286c is a dead terminal. Coil 286d is connected to output 184c and to terminal 140-8b and 140-9b so that when either contactor 140-8a or 140-9a is moved into contact with terminal 140-8b or 140-9b, respectively, relay coil 286d is energized and contactor 286a is moved into contact with terminal 286b. When contactor 286a is moved into contact with terminal 286b, the amplified output signal from amplifier 204 is transmitted to resistor 288. The output of amplifier 204 is also continuously connected through resistor 298 to the inverting input terminal 302-2 of amplifier 302. Resistor 288 is in turn connected in series to both condenser 290 and resistor 292. Condenser 290 is in turn connected to ground connection 296. Resistor 292 is in turn connected to the non-inverting input 294-3 of amplifier 294. Resistor 288 is preferably a 10,000 ohm resistor and resistor 292 is preferably 1,000,000 ohms. Condenser 290 is preferably 5.6 microfarads. Amplifier 294 is preferably an AD540 amplifier, as described above, having seven terminals 294-1 through 294-7. Terminals 294-1 and 294-5 are zero adjusting terminals connected through a potentiometer 304 to output 184b. Terminal 294-2 is the inverting input and terminal 294-6 is the output of amplifier 294. Terminals 294-4 and 294-7 are respectively connected to a −15 volt DC and a +15 volt DC source such as wires 280 and 282. The output terminal 294-6 is also connected to auto-zero switch 200 for selective transmission to the non-inverting input 302-3 of amplifier 302 through resistor 300 for differential comparison with the output from amplifier 204 transmitted to the inverting input 302-2 of amplifier 302. Amplifier 302 can also be an AD540 amplifier with seven terminals 302-1 through 302-7. Terminals 302-1 and 302-5 are zero adjusting terminals connected through potentiometer 306 to wire 282 in order to provide the proper voltage to terminals 302-1 and 302-5 to calibrate amplifier 302. Terminals 302-2 and 302-3 are the inverting and non-inverting terminals described above. Terminals 302-4 and 302-7 are connected respectively to wires 280 and 282 while terminal 302-6 is the output terminal of amplifier 302. Terminal 302-6 is continuously connected through a resistor 308 to the inverting input 310-2 of amplifier 310 of dilution compensation portion 276.

Dilution compensation portion 276 comprises bucking voltage generator 312 and amplifier 310. Amplifier 310 is preferably an AD540 amplifier with seven terminals 310-1 through 310-7. Terminals 310-1 and 310-5 are connected through a potentiometer 314 to wire 282 in order to provide proper voltage to terminals 310-1 and 310-5 to adjust amplifier 310. Terminals 310-2 and 310-3 are the inverting and non-inverting input terminals and terminals 310-4 and 310-7 are −15 volt DC and +15 volt DC terminals connected respectively to wires 280 and 282. Terminal 310-6 is the output terminal and is connected through resistor 316 to inverting input terminal 310-2 and separately to the input of potentiometers 134a and 134b. Amplifier 310 serves to provide an appropriate dilution compensated signal to potentiometers 134a and 134b which are in turn connected, as above described, to the DPM. Inverting input 310-2 is also connected to bucking voltage supply 312. Bucking voltage supply 312 comprises lead wires 318 and 320, potentiometers 322 and 324, ground connection 326, load resistors 328 and 330, DC voltage connector 332 and resistors 334 and 336. Lead wires 318 and 320 are respectively connected to terminals 140-10c and 140-11c so that when either contactor 140-10a or 140-11a is in its normal position in contact with terminal 140-10c or terminal 140-11c, respectively, the lead wire 318 and 320 is respectively grounded. Thus, if contactor 140-10a is in contact with terminal 140-10b so as to produce a calcium concentration reading, lead wire 318 is not grounded and a voltage signal generated from DC voltage connector 332 through resistor 328 and potentiometer 322 is allowed to pass ungrounded through resistor 336 to inverting input terminal 310-2 thereby offsetting the signal fed from output terminal 302-6 through resistor 308 to inverting input 310-2. This offset is the dilution compensation of the calcium signal and can be calibrated by adjustment of potentiometer 322. When contactor 140-11a is in contact with terminal 140-11b, lead wire 320 is not grounded and hence a signal generated by DC voltage connector 332 through resistor 330 and potentiometer 324 is allowed to pass ungrounded through resistor 334 to inverting input 310-2 to offset the signal transmitted from output terminal 302-6 to inverting input terminal 310-2. This offset is the dilution compensation of the magnesium signal and can be calibrated by adjustment of potentiometer 324. The magnesium dilution compensation passing through potentiometer 324 is calibrated on the basis of the amount of reagent 82 and solvent 44 which are added to the fixed volume of sample 110 in chamber 100 in order to achieve an accurate magnesium reading despite the dilution of the sample by solvent 44 and reagent 82. The calcium dilution compensation determined by potentiometer 322 is calibrated on the basis of the amount of Ca-Mg substitute 98 added to the sample 110 within detection chamber 100 during the magnesium analysis.

Referring again to FIG. 3, auto-service double-pole switch 200 comprises two contactors 200a and 201a, two auto position terminals 200b and 201b, two service position terminals 200c and 201c and a potentiometer 360. When contactor 200a is on terminal 200b, contactor 201 is on terminal 201a and when contactor 200a is on terminal 200c, contactor 201a is on terminal 201c. When switch 200 is in the auto position, i.e. with contactor 200a on terminal 200c, potentiometer 360 is connected through resistor 300 to the non-inverting input 302-3 of amplifier 302. Potentiometer 360 is also connected to a +15 volt DC source such as output 184b and to a −15 volt DC source such as output 184a, so that the voltage of the signal to input 302-3 can be varied by adjustment of potentiometer 360 to anywhere from 30 -volts DC to −15 volts DC. In this position the potentiometer is adjusted to zero the reading on the DPM 352 and printer 354. This is done when reagent 82 and solvent 44 are introduced to chamber 100, so as to calibrate the instrument for automatic operation. In this position, contactor 201a is in contact with terminal 201c which is in turn in contact with indicator light 128b. Contactor 201a is grounded so this contact grounds light 128b during the above zeroing of the DPM and printer. When contactor 201a is moved to the auto position in contact with auto position indicator 201b, the output 294-6 of auto-zero amplifier 294 is connected to the non-inverting input 302-3 of amplifier 302 so as to automatically zero the DPM reading when contactors 140-8a or 140-9a are in contact with terminal 140-8b or 140-9b respectively. This zeroing occurs first when reagent and solvent are added to chamber 100 and again following the initial magnesium reading and before the addition of Ca-Mg substitute solution 98. When contactor 200a is in this auto position, contactor 201a is in contact with dead terminal 201b.

FIG. 6 is a schematic electric diagram of the wiring interconnecting sampling and dispensing system 11a, terminal sets 162, 164 and 170 of control section 13a and printer 14. Also shown is terminal 172 of FIG. 3.

Terminal set 164 is connected to various parts of control section 13a as above described (see FIG. 3). Terminal set 164 is also connected to system 11a and printer 14 to form an interconnect system 340 which comprises terminal sets 164, 162 and 170 of control section 13a; terminal sets 342, 343 and 344 of system 11a; and terminal sets 348 and 350 of printer 14.

Terminal set 164 comprises 18 terminals 164-1 through 164-18, as noted above. Terminal sets 162 and 170 comprise four terminals 162-1 to 162-4 and 170-1 and 170-4. Terminal 162-4 and 170-4 are dead terminals, and therefore were omitted in FIG. 3 for clarity. Terminal set 172 contains three terminals for a three-wire 118 volt AC connection, as previously described. Terminal set 342 comprises ten terminals 342-1 to 342-10. Terminal set 344 comprises eight terminals 344-1 to 344-8. Terminal set 346 comprises ten terminals 346-1 to 346-10. Terminal sets 348 and 350 each comprise eight terminals 348-1 and 348-8 and 350-1 to 350-8, respectively.

Terminal 164-1 is connected to terminals 346-1, 348-1 and 350-1 while terminal 164-2 and 164-3 are connected to terminals 346-2, 348-3 and 350-3 to provide AC current to DPM 352, printer 354 and terminal sets 348 and 350. Terminals 164-2 and 164-3 are further connected to valves 36, 40, 56, 74, 104a and 104b and dispensers 88 and 96 via terminals 342-2 and 343-5 to provide a first wire connection of a two-wire AC supply to said valves and dispenser 172-3 is connected to said valves and dispensers by closing of selected ones of switches 140-1 through 140-7. Terminals 348-2, 350-2 and terminal 164-18 are grounded. Terminal 164-4 is connected via terminals 342-4 and 343-3 to valve 56 to provide the second wire of the two-wire AC circuit thereto when contactor 140-1a is in contact with terminal 140-1b. Terminal 164-5 and 6 are in contact with lamp 108 via terminals 344-7 and 344-8 to provide 6.3 volt AC current thereto when main power switch is turned on.

Terminals 164-7, 164-8, 164-9, 164-10 and 164-11 are connected to the solenoids of valve 104a, valve 36, valves 40 and 74, dispenser 88 and dispenser 96, respectively via terminals 342-5 and 343-1, 342-6, 342-7 and 343-2 and 343-4, 342-8, 342-9 and 342-10 to activate respective ones of said solenoids when selected ones of switches 140-1 to 140-6 are closed. As noted above, terminal 164-13 is blank and serves as an insulator and spacer between terminals 164-1 and 164-12, which handle AC current and terminals 164-14 to 164-18 which handle the photometer output and recorder input signals. Terminal 164-14 is connected through terminal 344-5 to the photometer anode (not shown). Terminal 164-15 and 164-16 are connected to the reference and measurement receivers 118 and 116 of photometric detector means 26a via 344-2 and 342-3, respectively. Terminals 344-1, 344-4 and 344-6 are blank spacers and insulator terminals. Terminals 164-17 and 164-18 are connected to the plus and minus inputs of DPM 352 via terminals.

Terminals 162-1 and 162-2 are connected to input terminals 346-8 and 346-9 of terminal set 346 of printer 354 and serve to provide the calcium or magnesium signal input thereto. Terminal 162-3 is connected to the plus sign input terminal 346-10. Terminals 346-3, 346-4 and 346-7 are blank insulating and spacing terminals.

Terminals 170-1 and 170-2 are connected to terminals 348-5 and 350-5, which are each the signal input terminals of four volt to amp signal transducers (not shown) for the magnesium and calcium concentration signals, respectively. Terminal 170-3 is grounded and is connected to terminals 348-6 and 350-6 to ground each set of four transducers. Terminals 348-7 and 348-8 transmit a magnesium signal to a remote signal receiver (not shown), such as an alarm bell, light or siren which is activated at a predetermined amperage proportional to and indicative of a magnesium concentration in excess of a predetermined limit. Similarly, terminals 350-7 and 350-8 transmit the transduced calcium signal to the remote signal receiver to indicate when an excessive calcium concentration is present. Terminals 348-4 and 348-50 are blank spacing and insulting terminals. Terminals 348-2 and 350-2 are grounded.

The operation of analyzer 10 or 10a will be evident to skilled artisans from the preceding structural disclosure, however the operation will be described in limited detail below for more clarity.

The use of diaphragm or membrane-type cells for the production of chlorine and caustic requires closer control of some metal ions in the feed brine than was previously necessary with mercury-type cells. Of particular concern are calcium and magnesium. As sodium is drawn across the diaphragm by electromotive force, caustic (NaOH) and hydrogen are formed by the reaction of the sodium ions with water. Any calcium or magnesium present in the brine will also be drawn through the diaphragm. These ions form larger, insoluble hydroxide molecules at the diaphragm-caustic interface. If the concentration of calcium and magnesium is high enough (above a few ppm) blinding, or plugging of the diaphragm will occur, resulting in a loss of efficiency and eventually requiring shut-down of the cell for diaphragm replacement.

To reduce the concentration of Ca and Mg in the feed brine, a treatment consisting of precipitation with caustic and carbonate, settling and filtering is used. To insure proper treatment of the brine, frequent analysis of the treated brine is required. The analyzers 10 and 10a described above were developed to provide rapid, accurate analyses of both Ca and Mg at the 0–10 ppm level.

Analyzer 10 or 10a preferably uses a fixed wavelength photometer to measure the color changes caused by the reaction of Ca or Mg with a reagent. A fixed volume of sample 62 is automatically drawn from the process stream and held for analysis while a predetermined fixed volume of diluting water and reagent are added to a detector chamber 100 of a photometric detector means 26 or 26a. After auto-zeroing the detector means 26 or 26a, the sample is added to the cell. The color change due to the presence of Mg in the sample causes a change in light intensity reaching the measurement receiver 116. The outputs of the measurement receiver 116 and reference receiver 118 are compared and their difference is amplified to produce an output voltage signal 220 which is amplified and scaled to read directly in parts per million Mg on a digital panel meter 352. The detector means 26 or 26a is again zeroed. Ca-Mg substitute 98 is added to the detector chamber 100. The color intensity will change if any Ca is present in the sample, and this change is shown on the DPM 352 directly in parts calcium per million parts of sample 62.

A digital printer 354 is used to make a permanent record of the Mg and Ca concentrations. A "+" sign is printed with the Mg readout to distinguish between the two analyses. The analyzer is shown in FIGS. 1–6.

The preferably corrosion-resistant sample-handling components can be mounted on a swing-out panel in a fiberglass housing, providing easy access for servicing, with a captive screw holding the panel in place during normal operation. A flow diagram is shown in FIGS. 1 and 2.

A fixed volume of sample (e.g. 8 ml) is trapped in a glass bulb by activation and deactivation of a three-way bypass valve. Sample and bypass rotameter-type flowmeters 51a and 51b can be used to indicate and adjust flows through the analyzer. A three-way sample drain valve 56a adds the sample to the photometer cell at the appropriate time as determined by timing section 120.

Valve 74 is a three-way solenoid valve. Activation of valve 74 adds a fixed volume (~20 ml) of reagent 82 to the chamber 100. Deactivation of the valve causes it to refill with reagent 82 via gravity feed.

Solvent chamber 38, fitted with valves 36 and 40, adds a fixed volume (~100 cc) of deionized water or other suitable solvent 44 to chamber 100 at the same time the reagent 82 is added. This preferably provides about a 5:1 dilution of the reagent, although other dilution ratios could be used. System 13 or 13a allows smaller volumes of reagent to be used, and extends the intervals between servicing.

Two injector pump dispensers 88 and 96 add other reagents 84, 92 to the photometer cell at the required time.

The photometer contains a light source, reference and measuring phototubes, narrow bandpass optical filters and the optical cell containing the reagent and sample. Detector means 26 and 26a provide a voltage change proportional to the concentration of calcium and magnesium present in their respective samples 62 by measuring the change in light intensity passing through their respective sample-reagent mixtures 110.

The control section 13 or 13a contains the power and measuring circuitry for sequential activation of the solenoid valves and detector means for automatic operation of the analyzer 10 or 10a.

Main power switch 180 applies power to the control and analyzer sections, DPM and the digital printer.

The three-position switches 158 and 160 (continuous, off, intermittent) apply power to the thirteen cam recycling timer 140, either directly or through a single cam frequency timer 142. In the continuous position, the multi-cam timer 140 runs continuously at some preset rate, e.g. 7½ minutes per cycle. In the intermittent position, the cycle is started periodically, for example at 15 to 60 minute intervals. The time intervals between cycles can be determined by the gear ratio chosen for the motor of the single-cam frequency timer 142.

A 5 ampere fuse (not shown) preferably protects the wiring in the event of a short or overload.

Potentiometers 134a and 134b are used to span or calibrate the analyzer. They attenuate the signal which is fed to the hold circuit 138 for continuous remote readout through the 4–20 mA transducers and also the digital panel meter 352 and printer 354 for local readout. The Ca or Mg light 128a or 128b above each potentiometer, respectively, is illuminated when the DPM 352 and printer 354 are displaying the respective Ca or Mg analysis. Adjusting the Ca or Mg potentiometer while the respective Ca of Mg light is on will change the display. If potentiometer 134a or 134b is adjusted when the associated light 128a or 128b is out, the change will show up during the next analysis.

The zero potentiometer 360 is used to balance the output of the measuring and reference phototubes. When switch 200 is in the service position and the detection chamber 100 is charged with diluted reagent, potentiometer 360 is adjusted until the DPM 352 reads zero. In the auto position, potentiometer 360 is disconnected from input 302-3 and the auto-zero circuit takes over the balancing function.

The DPM 352 provides a local readout of the Ca and Mg concentrations. During most of the analytical cycle, the input to the meter is shorted out, and a display of "00.0" is illuminated. When the Mg or Ca indicator light 128b or 128a is turned on through the multicam timer 140, a scaled photometer signal is fed to the DPM, reading in parts per million. The printer 354 makes a permanent record of both analyses and distinguishes between the two by printing a "+" sign with the Mg concentration.

The recycling multicam timer 140 controls the analytical sequence as follows: (referring to FIG. 2) Solenoids 104a and 56a and bypass valve 52a are energized, draining detection chamber 100 and filling the sample storage means 54. Shortly thereafter, solenoid valve 31 is energized, filling the solvent solenoids storage means 38 and rinsing the chamber 100. Valve 36 is then deactivated (i.e. closed) and solenoids 40 and 74 are then activated, dumping reagent 82 and diluting solvent 44 into the rinsed chamber 100. Dispenser 88 adds 1 cc of a masking agent 90, e.g. ascorbic acid solution, to chamber 100 and then the contents of chamber 100 are mixed by bubbling with air through activation of solenoid valve 104b. After a suitable period, the output signal 220 from amplifier 204 is stored as a zero signal by condensor 290.

The sample previously trapped in storage means 38 from the sample source is then added to the mixture 110 in chamber 100 via activation of solenoid 56 or 56a and mixed with air as previously described. The reagent 82 contains Calmagite. Any magnesium present in the sample will react with the Calmagite reagent, changing the reagent color from blue to purple (or to red if enough Mg is present). Because red filters 112 and 114 are used in the optics of detector means 26a, the changed reagent color will pass more light than the original blue reagent. The increased light striking the measurement receiver 116 causes a change in the voltage of signal 220. The new voltage is compared by amplifier 302 to the stored zero voltage, and the difference between the two is scaled by the Mg calibration potentiometer 134b and presented on the digital panel meter in parts per million Mg. The number presented on the DPM is printed by printer 354 on a paper tape for a permanent record.

The new output signal 220 is then stored as the new zero signal by condensor 290. Injector 96 is energized, adding a predetermined quantity, such as for example 1 cc, of a Ca-Mg substitute, such as for example a MgEDTA solution, to chamber 100. Any Ca present in chamber 100 due to the sample will displace the Mg in the Ca-Mg substitute, releasing an equivalent amount of Mg. The released Mg will react with the reagent (e.g. Calmagite) as described before, causing a color change toward red and increasing the photometer output signal. This signal is compared by amplifier 302 to the stored zero signal, spanned with the calcium calibration potentiometer and fed to the DPM and printer. The magnesium and calcium print-outs are distinguished by the "+" sign printed with the magnesium analysis.

Also, a voltage signal is generated by dilution compensator 226 to offset the Ca or Mg output from amplifier 302 by an amount regulated by potentiometers 332 and 324 to compensate for the dilution effect of the sample volume and masking agent volumes added.

While a preferred embodiment is described above, the skilled artisan will recognize that minor modifications can be made to the above embodiments without departing from the scope of the invention.

What is claimed is:

1. A method of monitoring calcium and magnesium mass concentrations of less than about 500 parts per million of solution in a liquid stream which comprises the steps of:
   (a) automatically introducing a fixed reactant volume of magnesium-free, calcium-free solution of indicator and solvent into a detection chamber;
   (b) automatically, colorimetrically analyzing said fixed volume of indicator and solvent to provide a first signal indicative of the absence of magnesium and calcium in said detection chamber;
   (c) automatically zeroing a display means responsive to said first signal;
   (d) automatically trapping a single fixed volume sample of liquid from said liquid stream;
   (e) automatically adding said fixed volume sample to said fixed reactant volume within said detection chamber to produce an initial change in the color inside said detection chamber;
   (f) automatically measuring said change in color to provide a second signal indicative of the concentration of magnesium in said sample;
   (g) automatically displaying said second signal in units of magnesium concentration on said display means;
   (h) automatically rezeroing said display means at the level of said magnesium concentration as determined by said second signal;
   (i) automatically adding a fixed volume of Ca-Mg substitute to said detection chamber so as to replace any calcium inside said detection chamber by a proportional additional amount of magnesium to produce an additional color change;
   (j) automatically measuring said additional color change to provide a third signal indicative of the concentration of calcium in said sample;
   (k) automatically displaying said third signal on said display means in units of calcium concentration;
   (l) automatically removing the contents of said detection chamber; and
   (m) automatically repeating steps (a) through (l) in sequence.

2. The method of claim 1, further comprising the step of offsetting said second and third signal by a preset amount to compensate for the dilution of said fixed volume of reagent by addition of said fixed volume of sample thereto.

3. The method of claim 1 wherein said liquid stream is a brine feed stream of an electrolytic cell for production of caustic soda and chlorine.

4. Apparatus for automatically monitoring calcium and magnesium concentrations of less than about 500 parts per million of solution in a sample source, which comprises:
   (a) a photometric detector means, having a detection chamber and a photometer, for colorimetrically analyzing a sample placed in said detection chamber and generating a detector output signal;
   (b) a sampling-reagents dispensing means, having:
      (i) sample supply means for intermittently trapping a fixed volume sample of liquid from said sample source and supplying said trapped sample to said detection chamber;
      (ii) indicator supply means for supplying a fixed volume of colorimetric indicator reagent to said detection chamber to react with said fixed volume sample to produce a color change indicative of the magnesium concentration in said sample liquid;
      (iii) masking agent supply means for supplying a fixed volume of masking agent to said detection chamber to minimize interference from other metal ions present in the fixed volume sample; and
      (iv) Ca-Mg substitute supply means, for supplying a fixed volume of Ca-Mg substitute to the contents of said detection chamber, so as to substitute additional magnesium ions for any calcium ions in the previously added contents of said detection chamber so as to produce an additional color change indicative of the calcium concentration in said sample source;
   (c) a display means for displaying a reading proportional to a display input signal supplied thereto; and
   (d) control section means, connected to each of said detector means, supply means and display means, for intermittently activating said detector means and supply means so as to generate separate detector output signals indicative of absence of calcium and magnesium, magnesium concentration, and the calcium plus magnesium concentration in said fixed volume of sample fluid and for converting said detector signals into display input signals and transmitting said display input signals to said display means and for automatically zeroing said display means prior to displaying each of a magnesium concentration signal and a calcium concentration signal.

5. The apparatus of claim 4 wherein said photometric detector means includes an air mixer means for slowly supplying air through said detector chamber in order to help mix said mixed contents thereof.

6. The apparatus of claim 4 wherein said control section further includes a timer section comprising:
   (a) multiple switch means for timing the sequence of operations of said detector means, each of said supply means and said display means to provide a calcium-magnesium analysis cycle;
   (b) frequency timer means for timing the frequency of operation of said multiple switch means so as to provide a selected time period between said calcium-magnesium analysis cycles; and
   (c) timer select switch means for selectively bypassing and inactivating said frequency timer means so as to provide continuous operation of said multiple switch means and selectively activating said frequency timer means so as to provide intermittent operation of said multiple switch means.

7. The apparatus of claim 6 wherein said sample supply means comprises:
   (a) connector means for fluidly communicating said sample supply means with said sample source;
   (b) sample storage means, in fluid communication with said conduit for storing a fixed volume of sample fluid;
   (c) a sample supply conduit connecting said connector means to said sample storage means;
   (d) a sample outlet conduit communicating said sample storage means with said detection chamber; and
   (e) a sample outlet shut-off valve for selectively opening and closing said sample outlet conduit responsive to a signal from said multiple switch means.

8. The apparatus of claim 6 wherein said control means further comprises auto-zero and compensation circuit section means for providing a reference detector output signal indicative of the amount of magnesium contributed by said masking agent, indicator reagent and any solvent to the contents of said detection chamber for use as a zero signal, for subsequent comparison against said separate detector output signals indicative of calcium and magnesium concentrations and for offsetting said detector output signals to compensate for the effect of dilution of the contents of said detector chamber by addition of said fixed volume of sample and subsequently said fixed volume of Ca-Mg substitute.

9. The apparatus of claim 4 wherein said display means further comprises:
   (a) digital panel meter means for displaying a digital reading in parts per million proportional to said display input signal, and
   (b) recorder means for recording separate said digital readings and indicating which readings are indicative of magnesium concentration and which are indicative of calcium concentration.

10. The apparatus of claim 4 wherein said sampling-reagents dispensing means further comprises a solvent supply means for supplying a fixed volume of solvent as a diluent to said detection chamber.

11. The apparatus of claim 10 wherein said solvent supply means comprises:
   (a) a connection means for connecting said solvent supply means to a source of solvent fluid;
   (b) a solvent storage means for storing a fixed volume of solvent;
   (c) a solvent supply conduit connecting said connector means to said solvent storage means;
   (d) a throttle valve means for regulating the flow rate of said solvent through said solvent supply conduit;
   (e) flowmeter means for measuring said flow rate through said solvent supply conduit;
   (f) a solvent supply shut-off valve means for allowing and preventing flow through said solvent supply conduit in response to a signal from said multiple switch means;
   (g) a solvent outlet conduit communicating said solvent storage means to said detector chamber;
   (h) a solvent outlet shut-off valve means for preventing and allowing flow through said solvent outlet conduit responsive to a signal from said multiple switch means; and
   (i) solvent drain means connected to said fixed volume storage means for limiting the amount of solvent in said storage means to a fixed volume when said solvent supply shut-off valve is open and said solvent outlet shut-off valve is closed.

12. The apparatus of claim 11 wherein said solvent drain means communicates with said detection chamber so as to rinse said detection chamber when fluid flows through said solvent drain means.

* * * * *